United States Patent
Tanner et al.

(10) Patent No.: US 9,121,046 B2
(45) Date of Patent: Sep. 1, 2015

(54) REDUCING TEMPLATE INDEPENDENT PRIMER EXTENSION AND THRESHOLD TIME FOR LOOP MEDIATED ISOTHERMAL AMPLIFICATION

(71) Applicant: New England Biolabs, Inc., Ipswich, MA (US)

(72) Inventors: Nathan Tanner, Peabody, MA (US); Thomas C. Evans, Jr., Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 248 days.

(21) Appl. No.: 13/671,123

(22) Filed: Nov. 7, 2012

(65) Prior Publication Data

US 2013/0122551 A1 May 16, 2013

Related U.S. Application Data

(60) Provisional application No. 61/560,518, filed on Nov. 16, 2011.

(51) Int. Cl.
*C12P 19/34* (2006.01)
*C12Q 1/68* (2006.01)

(52) U.S. Cl.
CPC ............... *C12P 19/34* (2013.01); *C12Q 1/6848* (2013.01)

(58) Field of Classification Search
CPC ........... C12Q 1/6848; C12Q 2522/101; C12Q 2527/101; C12Q 2527/125; C12Q 2531/119; C12P 19/34

USPC ......................................................... 435/91.2
See application file for complete search history.

(56) References Cited

U.S. PATENT DOCUMENTS

2014/0045221 A1* 2/2014 Cai et al. ...................... 435/91.5

OTHER PUBLICATIONS

Schlotterer and Tautz, Nucleic Acids Research, 20(2):211-215 (1992).
Ogata and Miura, Nucleic Acids Research, 26(20):4657-4661 (1998).
Shereda, et al. Critical reviews in Biochemistry and Molecular Biology, 43(5):289-318 (2008).
Brunker, et al. Analyitical Biochemistry, 339(2):345-347 (2005).
Notomi, et al. Nucleic Acids Research, 28(12):e63 (2000).
Nagamine, et al. Molecular and Cellular Probes, 16(3):223-229 (2002).
Tanner, et al. Biotechniques, 53(2):81-89 (2012).
Hamdan and Richardson, Annual Review of Biochemistry, 78:205-423 (2009).
Richard, et al. Critical Reviews in Biochemistry and Molecular Biology, 44(2-3):98-116 (2009).
Richard, et al. Nucleic Acids Research, 32(3):1065-1074 (2004).

* cited by examiner

*Primary Examiner* — Cynthia B Wilder
(74) *Attorney, Agent, or Firm* — New England Biolabs, Inc; Harriet M. Strimpel

(57) ABSTRACT

Compositions and methods are provided for loop mediated isothermal amplification in which single stranded binding proteins are shown to protect primers from non-specific extension and to stimulate the rate of threshold amplification.

6 Claims, 6 Drawing Sheets

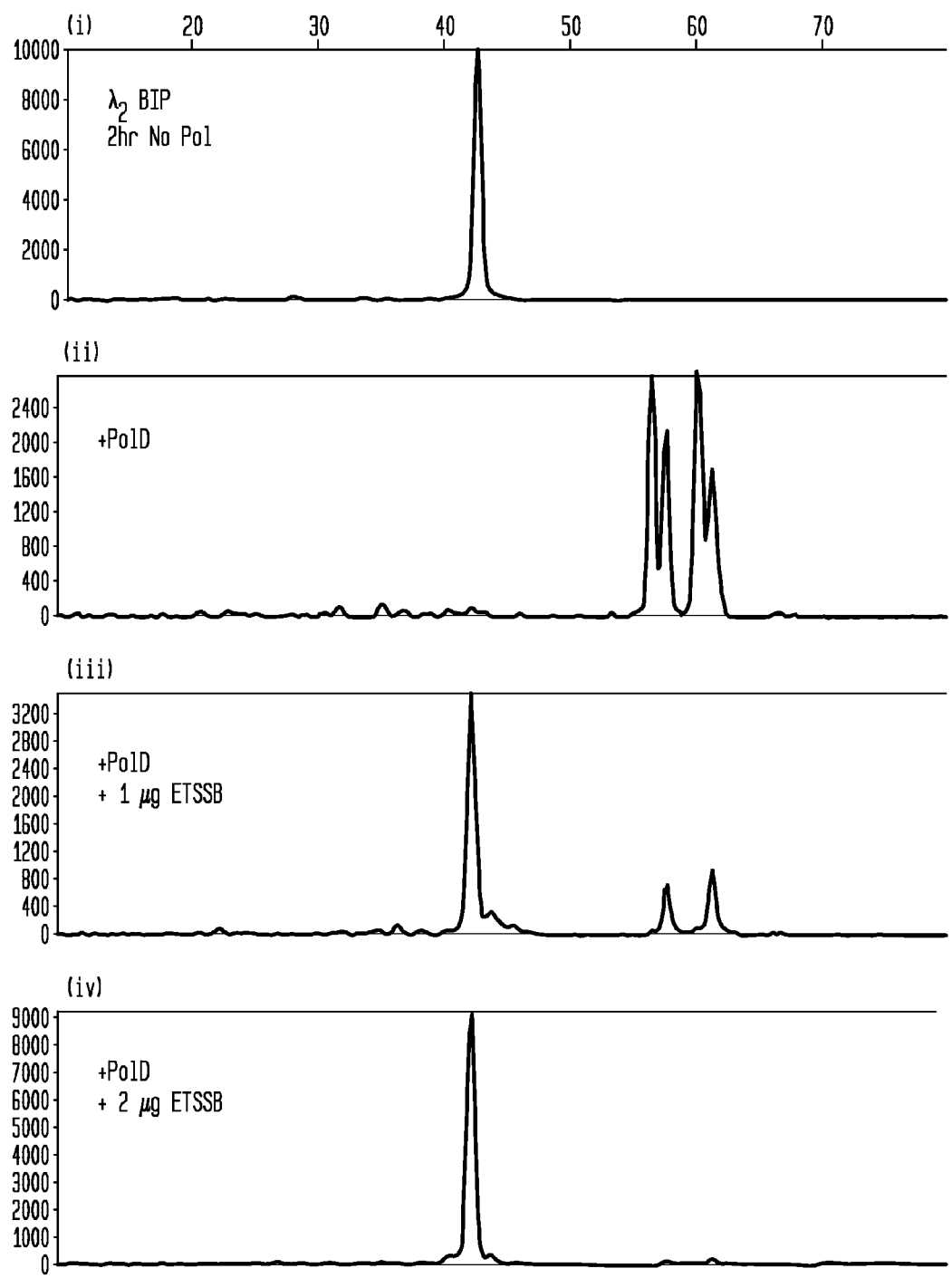

REDUCING TEMPLATE INDEPENDENT PRIMER EXTENSION AND THRESHOLD TIME FOR LOOP MEDIATED ISOTHERMAL AMPLIFICATION

BACKGROUND OF THE INVENTION

Amplification of target nucleic acids is a fundamental method in modern molecular biology and diagnostics. Factors that adversely affect the outcome of amplification reactions include: extension of primers due to non-specific template annealing during amplification, resulting in false positives (Schlotterer and Tautz, *Nucleic Acids Research*, 20(2):211-215 (1992); Ogata and Miura, *Nucleic Acids Research*, 26(20):4657-4661 (1998); Brukner, et al. *Analytical Biochemistry*, 339:345-347 (2005)); reduced amplification reaction efficiency and rate due to primer or template secondary structure; and variability of amplification due to primer dimer formation. The effects of these factors are enhanced by room temperature (RT) incubation of complete reaction mixtures prior to placement at specified reaction temperature. This would occur, for example, when large numbers of samples are prepared at one time necessitating a certain amount of sample incubation at RT. Therefore, high-throughput and diagnostic applications are often negatively impacted by reaction set-up at RT. This is a significant issue for molecular diagnostic applications, which, demands a high level of consistency and accuracy.

Various amplification methods are currently utilized in molecular diagnostics. A popular isothermal amplification diagnostic method is loop-mediated isothermal amplification (LAMP) (Notomi, et al. *Nucleic Acids Research*, 28(12):e63 (2000)). Typically, LAMP employs a DNA polymerase and a set of four to six synthetic primers that recognize a total of six distinct sequences on the target DNA. Recognizing six distinct sequences makes LAMP extremely specific for a target sequence. Despite the specificity of LAMP, it is adversely affected by unwanted, non-specific primer extension reactions during reaction set-up at RT.

SUMMARY

In general in one aspect, a preparation includes a SSB; a thermostable polymerase; at least four oligonucleotide primers, and a buffer.

In another aspect, the buffer in the preparation has a pH in the range of pH6-pH9, a monovalent salt having a concentration in the range of 0-500 mM, a divalent metal cation having a concentration of 0.5 mM-10 mM and optionally a stabilization agent selected from the group consisting of BSA, glycerol and detergent.

In another aspect, the SSB in the preparation is an extreme thermophile single strand binding protein (ET SSB) (New England Biolabs, Ipswich, Mass.).

In another aspect, the thermostable polymerase in the preparation has strand displacement activity and is active at temperatures of greater than 50° C.

In another aspect, the preparation is used in a method for amplifying a nucleic acid, which includes adding to the preparation, dNTPs and template nucleic acid; performing LAMP; and obtaining amplified template DNA.

In general in one aspect, a method for inhibiting primer extension of a primer in an amplification reaction, includes: combining a SSB with a thermostable polymerase, at least four primers and a template nucleic acid in a reaction buffer at a first temperature; performing a LAMP reaction at a second temperature which is greater than the first temperature; and determining the inhibition with respect to the same mixture without the SSB.

In another aspect, the method includes obtaining an increased rate of LAMP of the template DNA.

In general in one aspect, a method for obtaining an increase in a rate of LAMP, includes combining a SSB with a thermostable polymerase, at least four primers and a template nucleic acid in a reaction buffer at a first temperature; and immediately or after a lag time at a temperature above 4° C. but below 70° C., performing a LAMP reaction at a second temperature, wherein the increase is determined with respect to the same mixture without the SSB.

In another aspect, the increase in the rate of amplification is measured by time taken to reach threshold amplification is more than 25%.

After the pre-incubation, LAMP amplification was performed and the threshold time required to produce a threshold amount of fluorescent signal from a DNA intercalating dye was determined (see also Examples 1 and 2).

Figure 1A:
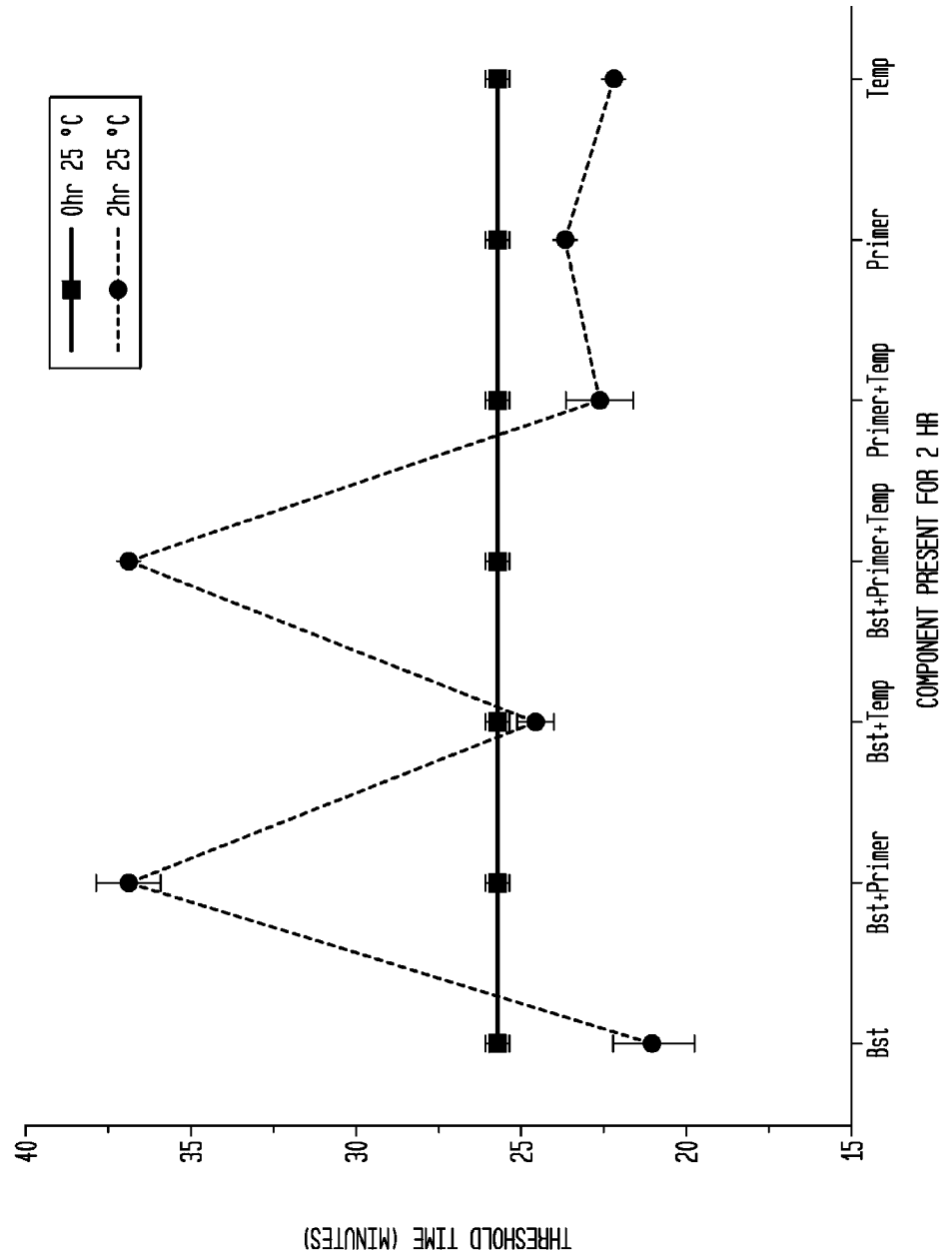
FIGS. 1A-B show the effect on amplification efficiencies when a LAMP reaction mixture (Notomi, et al. (2000)) was tested either immediately after removal of the sample from incubation on ice (solid line); or after a 2 hour pre-incubation of the sample at 25° C. before moving the sample to the 65° C. reaction temperature (dashed line).
Figure 1B:
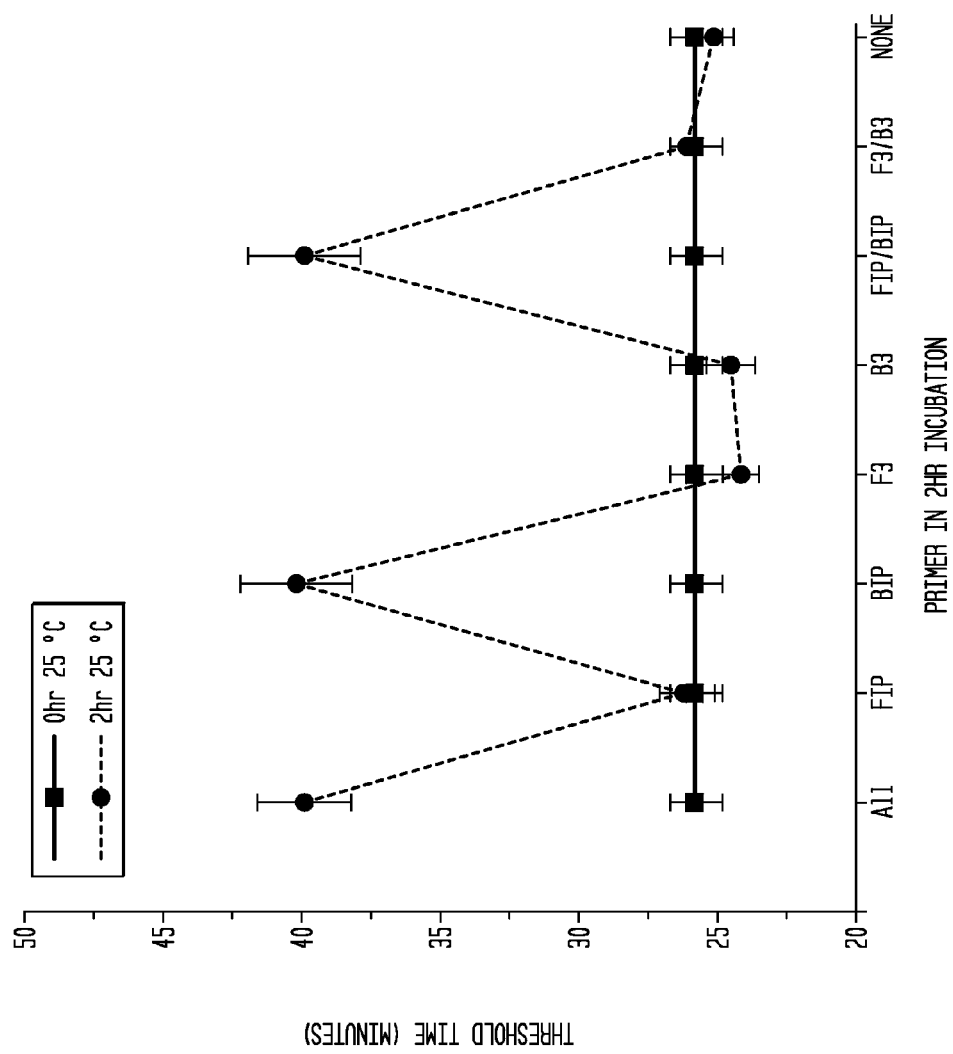

The results in FIGS. 1A and 1B showed that the reaction time to threshold signal for LAMP increased from 25 minutes for samples subjected to 0 hour pre-incubation at 25° C. to 40 minutes for the samples that had been subjected to a 2 hour pre-incubation at 25° C. for a reaction mixture containing Bst DNA polymerase, large fragment, and primers.

FIG. 1A shows results for reactions that contained LAMP primers, where the primers were forward internal primer (FIP), backward internal primer (BIP), forward external primer (F3) and backward external primer (B3). Results are shown for samples that contained Bst DNA polymerase, large fragment (Bst) only; Bst polymerase plus all primers; and Bst polymerase plus all primers plus lambda DNA template (temp). The deleterious effect of pre-incubation at 25° C. was observed for reactions that contained Bst polymerase and primers.

Figure 2A:
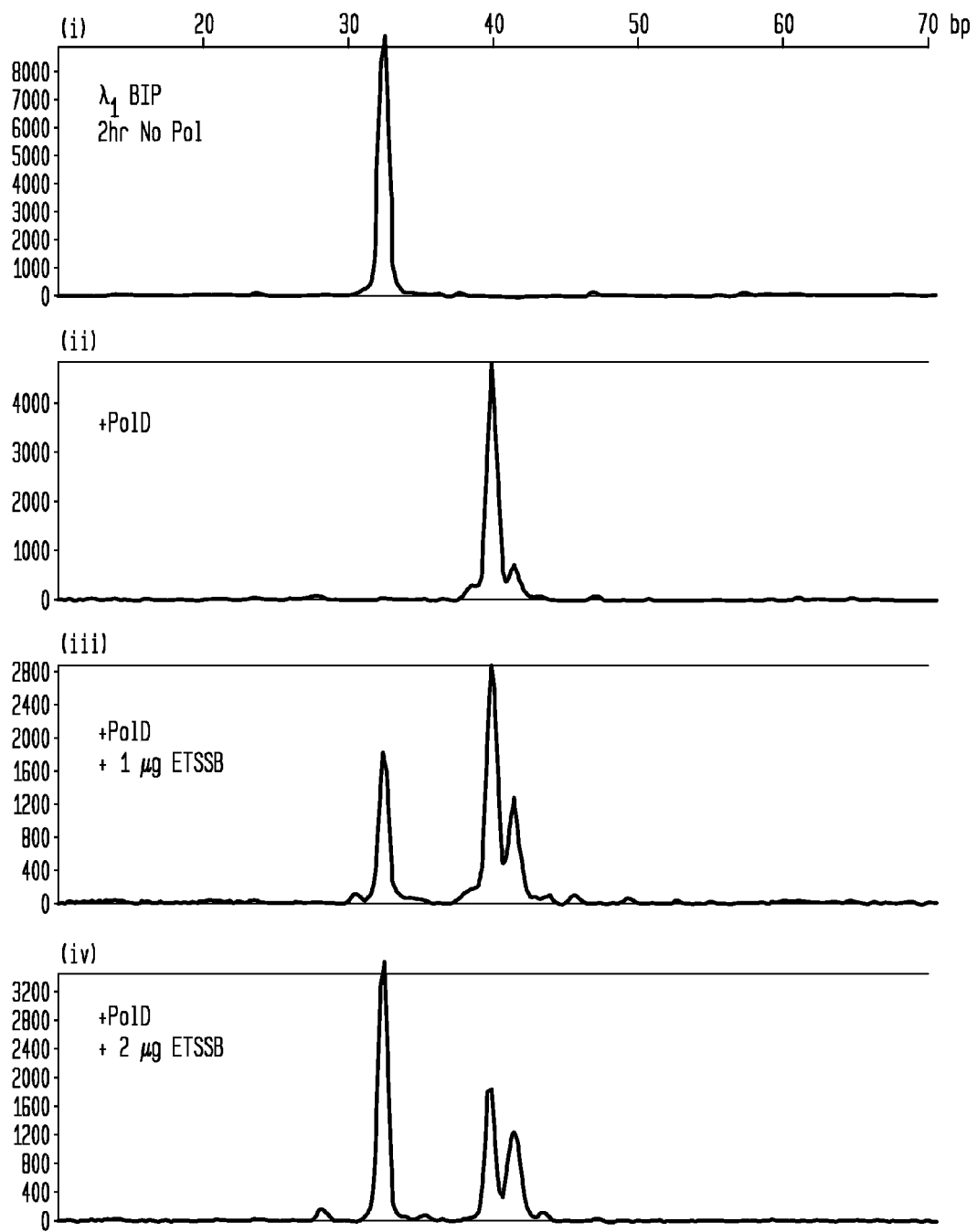

FIG. 1B shows the result of pre-incubation of Bst polymerase with specified LAMP primers (FIP; BIP; F3; B3; FIP+BIP; F3+B3; no primers or all primers) at 25° C. prior to the amplification reaction at 65° C. The deleterious effect of pre-incubation at 25° C. was observed for reactions that contained Bst polymerase and primers FIGS. 2A-B show capillary electrophoresis (CE) analysis of primer extension reactions that occurred at 25° C. The estimated number of nucleotides based on retention time in the CE is provided on the x-axis and the peak height in relative fluorescence units is given on the y-axis of each electropherogram. Primer extension was measured for individual primers in the presence or absence of an ET SSB. The results show that ET SSB is capable of protecting primers from undesirable extension reactions in the presence of a DNA polymerase, PolD, during LAMP reaction setup (2 hours at 25° C.). Template DNA was not included in the reaction. The observed protection was not primer specific as demonstrated in FIG. 2A, which utilized the BIP primer from the primer set described above and FIG. 2B which utilized a BIP from a different LAMP primer set.

The LAMP primers were incubated at 1.6 μM in reaction buffer as follows, with all reactions performed in 25 μL volumes:
(i) BIP primer, buffer, 2 hour incubation at 25° C. no ET SSB.
(ii) BIP primer, 10 U PoID polymerase, buffer, 2 hour incubation at 25° C., no ET SSB.
(iii) BIP primer, 10 U PoID polymerase, buffer, 2 hour incubation at 25° C., 1 μg ET SSB.
(iv) BIP primer, 10 U PoID polymerase, buffer, 2 hour incubation at 25° C., 2 μg ET SSB.

Subsequent to pre-incubation, the 1.6 μM samples were diluted to 5 nM and analyzed using CE. A CE peak can be seen in (i) indicating the unmodified primer, which in (ii) runs significantly larger, corresponding to the extension products of the fluorescently-labeled primer due to DNA polymerase activity. These extension peaks became diminished in the presence of the increasing amounts of SSB (iii and iv), indicating inhibition of extension of the primers at RT.

FIG. 2A shows data obtained using a 5'-FAM labeled lambda1 BIP primer from LAMP primer set used in FIGS. 1A-B, 3, and 4A-B (5'-6FAM-GAGAGAATTTGTACCAC-CTCCCACCGGGCACATAGCAGTCCTAGGGACA GT, IDT) (SEQ ID NO:1).

FIG. 2B shows data obtained using a 5'-FAM labeled lambda 2 BIP primer from a different set of LAMP primers (5'-6FAM-3') CAGGACGCTGTGGCATTGCAGATCAT-AGGTAAAGCGCCACGC (SEQ ID NO:2).

Figure 3:
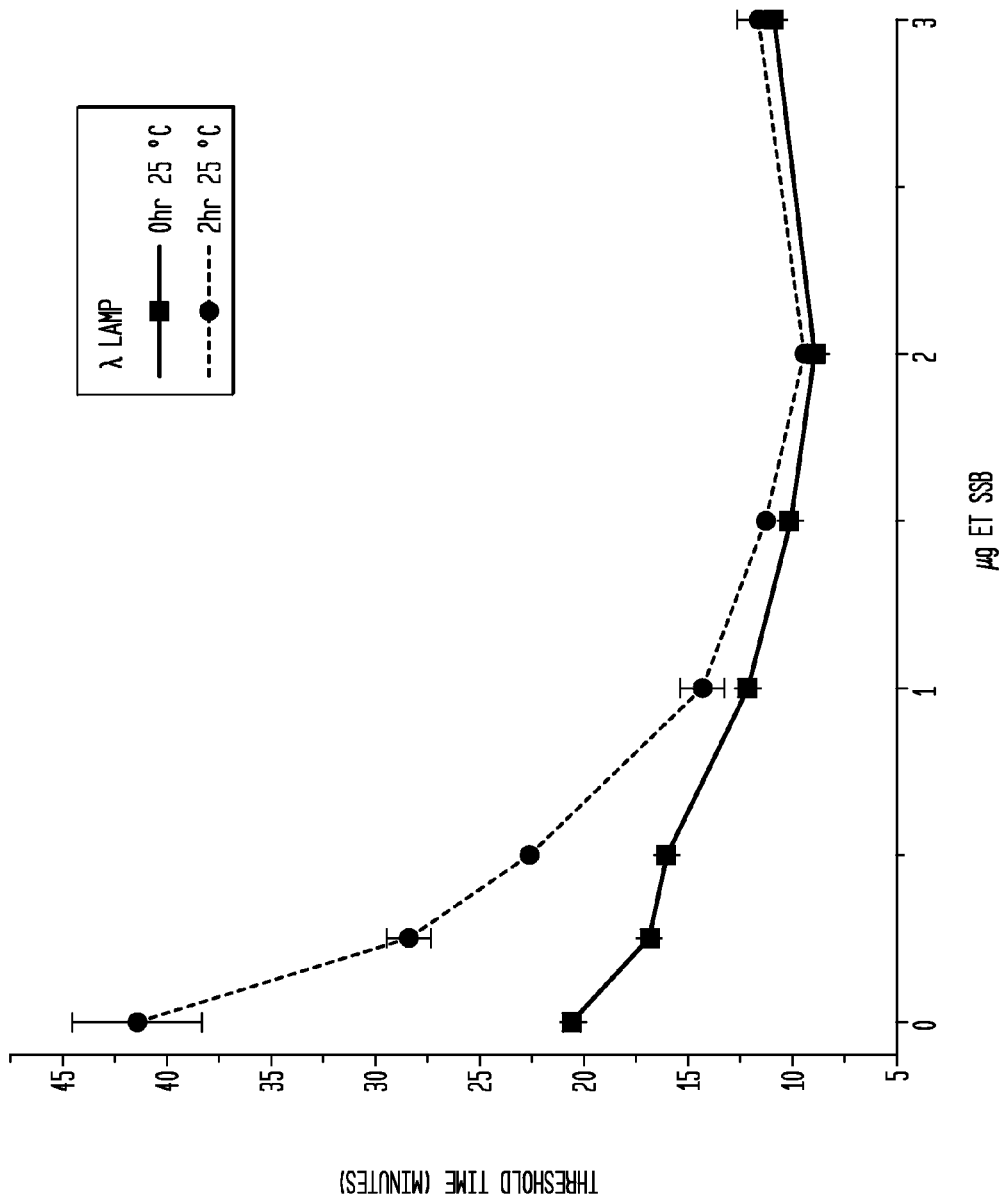

FIG. 3 shows the results of an assay for determining optimal amounts of ET SSB (1-3 μg) in the reaction mixture.

A single sample was divided into two aliquots. One aliquot was amplified immediately after removal from setup on ice (solid line). The second aliquot was amplified after the sample was pre-incubated at RT (25° C.) for 2 hours (dashed line). An increase in the rate of the amplification reaction as measured by a reduction in threshold time was observed, with the greatest stimulation observed above 1 μg ET SSB (reactions performed in 25 μL volume). The lag time between immediate (solid) and 2 hour incubated (dashed) samples also decreased, with an approximately 100% (20 minutes) delay observed without ET SSB, but no delay observed with 2 μg ET SSB. This demonstrates that ET SSB added to primers during the pre-incubation at RT enhanced amplification rates.

Figure 4A:
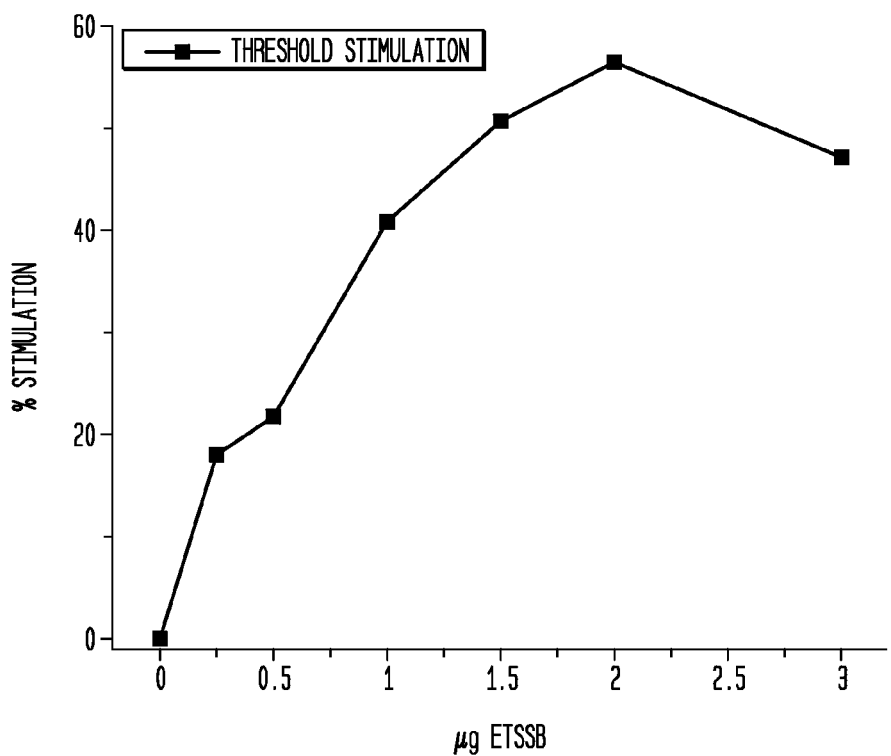
Figure 4B:
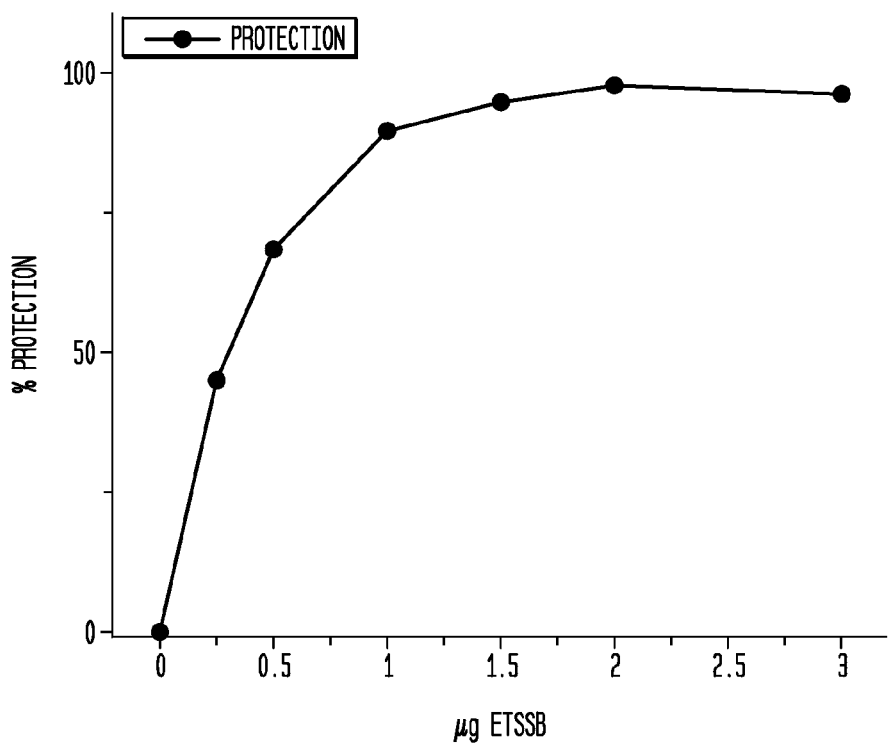

FIGS. 4A-B show the beneficial effect of ET SSB on threshold time for amplification and protection of primers from non-template extension.

FIG. 4A shows percent stimulation in threshold time for LAMP of target DNA when 0-3 μg ET SSB was added to primers prior to amplification (no incubation time). Concentrations of 1.5-3.0 μg ET SSB added to 25 μL reactions resulted in greater than 50% stimulation of amplification as measured by decreasing time to amplification threshold.

FIG. 4B shows the effect of 0-3 μg ET SSB on protection of primers from non-template extension due to pre-incubation at RT prior to performing LAMP reactions. 100% protection of the primers was achieved by use of 1-3 μg ET SSB added to 25 μL reactions. Protection was measured by difference between threshold times of the sample with no pre-incubation and the sample pre-incubated at RT for 2 hours, with no threshold time delay defined as 100% protection.

DESCRIPTION OF EMBODIMENTS

The problem of variability that arises from sample handling prior to amplification has been solved by the compositions and methods described herein. Primers combined with SSB that are allowed to stand at RT in the presence of polymerase are protected from undesired DNA polymerase dependent replication or extension in the absence of template DNA otherwise observed at temperatures lower than the amplification reaction temperature. This protection is not primer sequence dependent. The protective effect of SSBs results in one or more of the following benefits: reduced variability in threshold times for amplification, shorter times to reach threshold amplification and reduced lag time before amplification is initiated.

Generally, a stimulation of amplification reaction efficiency can decrease time to reach a defined threshold level of amplification, minimizing required reaction and diagnostic times. The beneficial effect of SSBs is observed when the time to reach the defined threshold is decreased. An increase in the rate of LAMP has been identified when SSBs are added to a buffer in which the reaction is subsequently performed. The increase in rate is measured by the time required to achieve a threshold yield of amplicon. The observed increase is at least 50% when SSB is added to a polymerase primer mix at, for example, one to two molar equivalents of the DNA primers or for example 0.5-10 μg, 1.0-5 μg or 1.5-3.0 μg of SSB.

Threshold times may be based on sufficient amplification to produce a detectable signal, for example, a fluorescent signal with an intercalating dye on a real time fluorimeter in the range of 100-500,000 RFU, preferably at least 1000 RFU. Alternatively, turbidity methods can be used where threshold is defined as dT/dt greater than 0.1.

In addition to stimulation of reaction time efficiency, protection from non-template primer extension is also provided by the SSB. While the protection from non-template primer extension is not primer dependent and is observed for primers regardless of sequence, some variation in the extent of protection may occur. However, in all cases, the benefit is significant. The protection can range from 25% to 100% where 100% protection is equivalent to the optimal efficiency of amplification when a sample is removed from a 4° C. environment and immediately amplified without any RT incubation and 0% is the protection against non-template primer extension afforded after a pre-incubation of primers with polymerase for 2 hours at 25° C. in the absence of SSB (see FIGS. 2A-B and 4A-B).

Protection can be achieved when an SSB is added to a polymerase primer mix at, for example, one to two molar equivalents of the DNA primers or for example 0.5-10 μg, 1.0-5 μg or 1.5-3.0 μg of SSB in a 25-50 μl reaction.

The addition of SSB protects against the negative consequences of RT setup of amplification reactions prior to raising the temperature to initiate amplification as the SSB prevents primer extension to an extent of at least 25%, 30%, 35%, 40%, 45%, 50%, 55%, 60%, 65%, 70%, 75%, 80%, 85%, 90% or 95%. The pre-incubation time although exemplified as 2 hours at RT could be as little as 5 minutes or as much as 24 hours. The pre-incubation temperature although exemplified by 25° C. is intended to include any temperature greater than 4° C. and less than 50° C.

The present methods and compositions can be used for a hot start amplification in which any non-template primer extension is blocked at RT in the presence of SSB prior to raising the temperature to 50° C.-70° C. in an isothermal reaction such as LAMP.

As described above, the protection of primers from extension by SSB under these conditions gives rise to stimulation of amplification efficiency and reduced variability in amplification reactions and enhances reaction performance.

Examples of SSBs known in the art that may be used in the present methods and compositions include: bacterial SSBs (e.g. *E. coli* SSB) and phage SSBs (T4 gp32, T7 gp2.5) (Hamdan and Richardson, *Annual Review of Biochemistry*, 78:205-243 (2009)). SSBs from eukaryotic organisms (e.g. RPA) have similar mechanisms of action and interaction in DNA replication and repair processes (Richard, et al. *Critical Reviews in Biochemistry and Molecular Biology,* 44 (2-3):98-116, (2009)) and may be used herein. While a thermostable SSB is exemplified here, this is not intended to be limiting.

ET SSB is a 16 kDa single-stranded DNA binding protein which is fully active after 60 minutes at 95° C. and can destabilize secondary structure, and improve DNA polymerase activity (Richard, et al. *Nucleic Acids Research,* 32 (3):1065-1074, (2004)). The ET SSB can be used for hot start amplification and for PCR, RT-PCR, HDA, RCA, sequencing, and isothermal amplification reactions.

Thermostable polymerases for use in LAMP include PoID; Bst DNA polymerase large fragment; mutants thereof; or WarmStart™ Bst 2.0 DNA polymerase (New England Biolabs, Ipswich, Mass.) (Notomi et al. (2000); Tanner, et al., *BioTechniques,* 53:81-89, (2012)).

TABLE 1

Examples of oligonucleotides (LAMP primers) showing similar protection and threshold stimulation to that shown in FIGS. 3, 4A and 4B for SEQ ID NOs: 1 and 2.

| Target | | Primer Sequence |
|---|---|---|
| lambda 1 | FIP | CAGCCAGCCGCAGCACGTTCGCTCATAGGAGATATGGT AGAGCCGC (SEQ ID NO: 3) |
| | BIP | GAGAGAATTTGTACCACCTCCCACCGGGCACATAGCAG TCCTAGGGACAGT (SEQ ID NO: 1) |
| | F3 | GGCTTGGCTCTGCTAACACGTT (SEQ ID NO: 4) |
| | B3 | GGACGTTTGTAATGTCCGCTCC (SEQ ID NO: 5) |
| | Loop F | CTGCATACGACGTGTCT (SEQ ID NO: 6) |
| | Loop B | ACCATCTATGACTGTACGCC (SEQ ID NO: 7) |
| lambda 2 | FIP | AGGCCAAGCTGCTTGCGGTAGCCGGACGCTACCAGCT TCT (SEQ ID NO: 8) |
| | BIP | CAGGACGCTGTGGCATTGCAGATCATAGGTAAAGCGCC ACGC (SEQ ID NO: 2) |
| | F3 | AAAACTCAAATCAACAGGCG (SEQ ID NO: 9) |
| | B3 | GACGGATATCACCACGATCA (SEQ ID NO: 10) |
| | Loop F | GCATCCCACCAACGGGAA (SEQ ID NO: 11) |
| | Loop B | CAGATTAAGGA (SEQ ID NO: 12) |
| lambda C | FIP | CGAACTGTTTCGGGATTGCATTCTGGAACTCCAACCAT CGCA (SEQ ID NO: 13) |
| | BIP | GGAGCCTGCATAACGGTTTCGTCGACTCAATGCTCTTA CCTGT (SEQ ID NO: 14) |
| | F3 | GTTGGTCACTTCGACGTATCG (SEQ ID NO: 15) |
| | B3 | GCTCGCCGACTCTTCACGAT (SEQ ID NO: 16) |
| | Loop F | TTTGCAGACCTCTCTGCC (SEQ ID NO: 17) |
| | Loop B | GGATTTTTTATATCTGCACA (SEQ ID NO: 18) |
| E. coli dnaE | FIP | CTGCCCCGACGATAGGCTTAATCGTGGTCTGGTGAAGT TCTACGG (SEQ ID NO: 19) |
| | BIP | TCCAGTGCGACCTGCTGGGTGGGTATTGTTCGCCGCC AGTAC (SEQ ID NO: 20) |
| | F3 | GATCACCGATTTCACCAACC (SEQ ID NO: 21) |
| | B3 | CTTTTGAGATCAGCAACGTCAG (SEQ ID NO: 22) |
| | Loop F | TGCGCCATGTCCCGCT (SEQ ID NO: 23) |
| | Loop B | TGAGTTAACCCACCTGACG (SEQ ID NO: 24) |
| C. elegans lec-6 | FIP | TGTTAAGGCGGACTGTGTTCGTCAAACCGCAACGAGAC AGTCT (SEQ ID NO: 25) |
| | BIP | CCGAGATAATTCCACCGTTGGATCCATTCCAGCAGAAC AAGAT (SEQ ID NO: 26) |
| | F3 | GATGTCACGAAAAATTCCCTC (SEQ ID NO: 27) |
| | B3 | GCAATCCGAGGATCGTCAC (SEQ ID NO: 28) |
| | Loop F | TGCAAAGCACGTGGTGCC (SEQ ID NO: 29) |
| | Loop B | ACACAAACTCCAGAGTGTAG (SEQ ID NO: 30) |
| C. elegans lec-10a | FIP | CTCTGTGAACGGTCATCACCTCGATGGCTTGAACCGAT TGGTATGG (SEQ ID NO: 31) |
| | BIP | CTTACATGGTAATATCCAGCGTGCCACTTCACCACTCG GAGCAC (SEQ ID NO: 32) |
| | F3 | GAACGTCTCCCTTCAATCC (SEQ ID NO: 33) |
| | B3 | GGACCAGAAATCCGTCACA (SEQ ID NO: 34) |
| | Loop F | CCGACTACCCACATCGTTAC (SEQ ID NO: 35) |
| | Loop B | ACCTTGATGCTAAGGTGGAA (SEQ ID NO: 36) |
| C. elegans lec-10b | FIP | GATTCCACTTCCAACGTCGTTG-CATAGGCATTGTATCCAGAGTG (SEQ ID NO: 37) |
| | BIP | CGAAGTGAACCTTGTCAACATGAGACTACCCACATCGT TACC (SEQ ID NO: 38) |
| | F3 | AGCAACATAGGTTTCAGTTC (SEQ ID NO: 39) |
| | B3 | CTGTGAACGGTCATCACC (SEQ ID NO: 40) |
| | Loop F | ACGGACATGTCGATCATGGA (SEQ ID NO: 41) |
| | Loop B | CGTCTCCCTTCAATCCGATGGC (SEQ ID NO: 42) |

TABLE 1-continued

Examples of oligonucleotides (LAMP primers) showing similar protection and threshold stimulation to that shown in FIGS. 3, 4A and 4B for SEQ ID NOs: 1 and 2.

| Target | | Primer Sequence |
|---|---|---|
| pUC19 AmpR | FIP | ATGGGGGATCATGTAACTCGCCTCGTCGTTTGGTATGG CTTC (SEQ ID NO: 43) |
| | BIP | AAGCGGTTAGCTCCTTCGGTCTGCTGCCATAACCATGA GTG (SEQ ID NO: 44) |
| | F3 | CTACAGGCATCGTGGTGTC (SEQ ID NO: 45) |
| | B3 | CTTACGGATGGCATGACAGT (SEQ ID NO: 46) |
| | Loop F | TGGGAACCGGAGCTGAAT (SEQ ID NO: 47) |
| | Loop B | TCCGATCGTTGTCAGAAGTAAGTTG (SEQ ID NO: 48) |
| Human CFTR | FIP | CCAAAGAGTAAAGTCCTTCTCTCTCGAGAGACTGTTGG CCCTTGAAGG (SEQ ID NO: 49) |
| | BIP | GTGTTGATGTTATCCACCTTTTGTGGACTAGGAAAACAG ATCAATAG (SEQ ID NO: 50) |
| | F3 | TAATCCTGGAACTCCGGTGC (SEQ ID NO: 51) |
| | B3 | TTTATGCCAATTAACATTTTGAC (SEQ ID NO: 52) |
| | Loop F | ATCCACAGGGAGGAGCTCT (SEQ ID NO: 53) |
| | Loop B | CTCCACCTATAAAATCGGC (SEQ ID NO: 54) |
| Human BRCA-1 | FIP | GGGCGTGGTAGCGCAGACCAGTCAAGTGATCCTCCTG CCTCAG (SEQ ID NO: 55) |
| | BIP | GAGGTTTCCCTATGTTGCCCAGGCCCAAAGTTCAAGGA TCACTTGG (SEQ ID NO: 56) |
| | F3 | CAGCCTCAACCTCCTGGGC (SEQ ID NO: 57) |
| | B3 | TAATCCCAGCATTTTGGGAG (SEQ ID NO: 58) |
| | Loop F | GGTCCCAGCTATTTGGAAGG (SEQ ID NO: 59) |
| | Loop B | TGGTCTTGAACTTCTGGGC (SEQ ID NO: 60) |

All references cited herein, as well as U.S. provisional application Ser. No. 61/560,518 filed Nov. 16, 2011, are hereby incorporated by reference.

EXAMPLES

Example 1

Determination of the Difference in Time to Reach Threshold Amplification Levels for Samples Pre-Incubated at RT Prior to Amplification with LAMP Primers in the Absence of SSB Compared with Samples that are Amplified without Pre-Incubation LAMP reactions were performed at 65° C. either immediately or with indicated components incubated for 2 hours at 25° C. Reactions were performed in 25 µL volumes and consisted of 8 U Bst DNA Polymerase (New England Biolabs, Ipswich, Mass.), 5 ng λ DNA (New England Biolabs, Ipswich, Mass.), and LAMP primers used together or separately as shown in FIGS. 1A and 1B.

Primers:

(1.6 µM FIP
(SEQ ID NO: 3)
5'-CAGCCAGCCGCAGCACGTTCGCTCATAGGAGATATGGTAGAGCCGC;

1.6 µM BIP
(SEQ ID NO: 1)
5'GAGAGAAATTTGTACCACCTCCCACCGGGCACATAGCAGTCCTAGGGAC
AGT;

0.2 µM F3
(SEQ ID NO: 4)
5'-GGCTTGGCTCTGCTAACACGTT;

and 0.2 µM B3
(SEQ ID NO: 5)
5'-GGACGTTTGTAATGTCCGCTCC).

The primers (Integrated DNA Technologies, Coralville, Iowa) were added to an amplification buffer (20 mM Tris, 10 mM KCl, 10 mM $(NH_4)_2SO_4$, 2 mM $MgSO_4$, pH 8.8 25° C.) (New England Biolabs, Ipswich, Mass.) and supplemented with additional 6 mM $MgSO_4$, 0.01% Tween-20 and 1.4 mM dNTPs.

The results are shown in FIGS. 1A-B.

A lag time of about 15 minutes to reach threshold levels of amplification was calculated in the sample subjected to 2 hour pre-incubation before LAMP reached the threshold value. This decrease in efficiency occurred only when the reaction was incubated in the presence of primers and DNA polymerase, indicating unwanted activity of DNA polymerase on primers at RT.

Example 2

Protection of Primers Using SSB from Non-Templated Extension by DNA Polymerase

Single LAMP primers with 5'-conjugated fluorophores were incubated at RT for 2 hours under various conditions to demonstrate non-template addition by DNA polymerase and inhibition of this extension by SSB. The primers were incubated at 1.6 µM in amplification buffer as follows, with all reactions performed in 25 µL volumes:
(i) BIP primer (from set 1 or 2), amplification buffer, 2 hour incubation at 25° C. no ET SSB.
(ii) BIP primer, 10 U PoID polymerase, amplification buffer, 2 hour incubation at 25° C., no ET SSB.

(iii) BIP primer, 10 U PoID polymerase, amplification buffer, 2 hour incubation at 25° C., 1 μg ET SSB.
(iv) BIP primer, 10 U PoID polymerase, amplification buffer, 2 hour incubation at 25° C., 2 μg ET SSB.

Subsequent to pre-incubation, the primers were diluted to 5 nM and analyzed using CE (FIGS. 2A-B). FIGS. 2A-B shows that the unmodified primer (i) becomes extended in length when a polymerase is added over the indicated pre-incubation period (ii). This corresponds to the extension products of the fluorescently-labeled primer due to DNA polymerase activity. These extension peaks became diminished in the presence of the increasing amounts of SSB (iii and iv), indicating inhibition of extension of primer in the absence of template. FIG. 2A shows data obtained using a 5'-FAM labeled lambda BIP primer (from primer set 1, see Example 1) and FIG. 2B shows data obtained using a 5'-FAM labeled lambda BIP primer (from set 2), demonstrating that non-template primer extension and SSB protection are not limited to a specific primer sequence.

Example 3

Determining Optimum Amount of ET SSB for Stimulating Amplification Rate and Protection from Non-Templated Primer Extension LAMP reactions were set up using 1.6 μM FIP and BIP, and 0.2 μM F3 and B3 plus 5 ng λ DNA in a buffer containing 20 mM Tris, 10 mM KCl, 10 mM $(NH_4)_2SO_4$, 2 mM $MgSO_4$, pH 8.8 25° C. supplemented with additional 6 mM $MgSO_4$, 0.01% Tween-20 and 1.4 mM dNTPs. Reactions were all 25 μL, contained 10 U Polymerase D, and were incubated at 65° C. Threshold time was defined by fluorescence measurement in Bio-Rad CFX96™ (Bio-Rad, Hercules, Calif.) due to presence of 2 μM SYTO-9® intercalating dye (Life Technologies, Grand Island, N.Y.). The resulting amplification threshold times are shown in FIG. 3. The results are shown in FIGS. 3 and 4A-B.

What is claimed is:

1. A method for increasing the rate of a loop mediated isothermal amplification (LAMP) reaction, comprising:
   (a) combining a single-stranded binding protein (SSBP), a thermostable polymerase, at least four primers, dNTPs and a template nucleic acid in a reaction buffer at a first temperature wherein the first temperature is greater than 4° C. and less than 50° C.; and
   (b) amplifying the template nucleic acid by LAMP at a second temperature that is greater than the first temperature, wherein the presence of the SSBP decreases non-templated primer extension and increases the rate of the LAMP reaction.

2. The method of claim 1, wherein the SSBP is thermostable.

3. The method of claim 1, wherein the thermostable polymerase is Bst DNA polymerase large fragment or a mutant thereof.

4. The method of claim 1, wherein the at least four primers is six primers.

5. The method of claim 1, wherein the second temperature in the range of 50° C. to 70° C.

6. The method of claim 1, wherein the method comprises incubating the product of step (a) at a temperature of greater than 4° C. and less than 50° C. for a period of time in the range of 5 minutes to 24 hours, prior to step (b).

* * * * *

SEQUENCE LISTING

```
<160> NUMBER OF SEQ ID NOS: 60

<210> SEQ ID NO 1
<211> LENGTH: 51
<212> TYPE: DNA
<213> ORGANISM: Artificial Sequence
<220> FEATURE:
<223> OTHER INFORMATION: Synthetic construct

<400> SEQUENCE: 1
gagagaattt gtaccacctc ccaccgggca catagcagtc ctagggacag t          51

<210> SEQ ID NO 2
<211> LENGTH: 42
<212> TYPE: DNA
<213> ORGANISM: Artificial Sequence
<220> FEATURE:
<223> OTHER INFORMATION: Synthetic construct

<400> SEQUENCE: 2
caggacgctg tggcattgca gatcataggt aaagcgccac gc                    42

<210> SEQ ID NO 3
<211> LENGTH: 46
<212> TYPE: DNA
<213> ORGANISM: Artificial Sequence
<220> FEATURE:
<223> OTHER INFORMATION: Synthetic construct

<400> SEQUENCE: 3
cagccagccg cagcacgttc gctcatagga gatatggtag agccgc                46

<210> SEQ ID NO 4
<211> LENGTH: 22
<212> TYPE: DNA
<213> ORGANISM: Artificial Sequence
<220> FEATURE:
<223> OTHER INFORMATION: Synthetic construct

<400> SEQUENCE: 4
ggacgtttgt aatgtccgct cc                                          22

<210> SEQ ID NO 5
<211> LENGTH: 22
<212> TYPE: DNA
```

```
<213> ORGANISM: Artificial Sequence
<220> FEATURE:
<223> OTHER INFORMATION: Synthetic construct

<400> SEQUENCE: 5
ggacgtttgt aatgtccgct cc                                              22

<210> SEQ ID NO 6
<211> LENGTH: 17
<212> TYPE: DNA
<213> ORGANISM: Artificial Sequence
<220> FEATURE:
<223> OTHER INFORMATION: Synthetic construct

<400> SEQUENCE: 6
ctgcatacga cgtgtct                                                    17

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
accatctatg actgtacgcc                                                 20

<210> SEQ ID NO 8
<211> LENGTH: 40
<212> TYPE: DNA
<213> ORGANISM: Artificial Sequence
<220> FEATURE:
<223> OTHER INFORMATION: Synthetic construct

<400> SEQUENCE: 8
aggccaagct gcttgcggta gccggacgct accagcttct                           40

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
aaaactcaaa tcaacaggcg                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
gacggatatc accacgatca                                                 20

<210> SEQ ID NO 11
<211> LENGTH: 18
<212> TYPE: DNA
<213> ORGANISM: Artificial Sequence
<220> FEATURE:
<223> OTHER INFORMATION: Synthetic construct

<400> SEQUENCE: 11
gcatcccacc aacgggaa                                                   18
```

<210> SEQ ID NO 12
<211> LENGTH: 11
<212> TYPE: DNA
<213> ORGANISM: Artificial Sequence
<220> FEATURE:
<223> OTHER INFORMATION: Synthetic construct

<400> SEQUENCE: 12
cagattaagg a                                                                 11

<210> SEQ ID NO 13
<211> LENGTH: 42
<212> TYPE: DNA
<213> ORGANISM: Artificial Sequence
<220> FEATURE:
<223> OTHER INFORMATION: Synthetic construct

<400> SEQUENCE: 13
cgaactgttt cgggattgca ttctggaact ccaaccatcg ca                                42

<210> SEQ ID NO 14
<211> LENGTH: 43
<212> TYPE: DNA
<213> ORGANISM: Artificial Sequence
<220> FEATURE:
<223> OTHER INFORMATION: Synthetic construct

<400> SEQUENCE: 14
ggagcctgca taacggtttc gtcgactcaa tgctcttacc tgt                               43

<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
gttggtcact tcgacgtatc g                                                      21

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
gctcgccgac tcttcacgat                                                        20

<210> SEQ ID NO 17
<211> LENGTH: 18
<212> TYPE: DNA
<213> ORGANISM: Artificial Sequence
<220> FEATURE:
<223> OTHER INFORMATION: Synthetic construct

<400> SEQUENCE: 17
tttgcagacc tctctgcc                                                          18

<210> SEQ ID NO 18
<211> LENGTH: 20
<212> TYPE: DNA
<213> ORGANISM: Artificial Sequence
<220> FEATURE:

<223> OTHER INFORMATION: Synthetic construct

<400> SEQUENCE: 18
ggatttttta tatctgcaca                                                     20

<210> SEQ ID NO 19
<211> LENGTH: 45
<212> TYPE: DNA
<213> ORGANISM: Artificial Sequence
<220> FEATURE:
<223> OTHER INFORMATION: Synthetic construct

<400> SEQUENCE: 19
ctgccccgac gataggctta atcgtggtct ggtgaagttc tacgg                         45

<210> SEQ ID NO 20
<211> LENGTH: 42
<212> TYPE: DNA
<213> ORGANISM: Artificial Sequence
<220> FEATURE:
<223> OTHER INFORMATION: Synthetic construct

<400> SEQUENCE: 20
tccagtgcga cctgctgggt gggtattgtt cgccgccagt ac                            42

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
gatcaccgat ttcaccaacc                                                     20

<210> SEQ ID NO 22
<211> LENGTH: 22
<212> TYPE: DNA
<213> ORGANISM: Artificial Sequence
<220> FEATURE:
<223> OTHER INFORMATION: Synthetic construct

<400> SEQUENCE: 22
cttttgagat cagcaacgtc ag                                                  22

<210> SEQ ID NO 23
<211> LENGTH: 16
<212> TYPE: DNA
<213> ORGANISM: Artificial Sequence
<220> FEATURE:
<223> OTHER INFORMATION: Synthetic construct

<400> SEQUENCE: 23
tgcgccatgt cccgct                                                         16

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
tgagttaacc cacctgacg                                                      19

<210> SEQ ID NO 25
<211> LENGTH: 43
<212> TYPE: DNA
<213> ORGANISM: Artificial Sequence
<220> FEATURE:
<223> OTHER INFORMATION: Synthetic construct

<400> SEQUENCE: 25
tgttaaggcg gactgtgttc gtcaaaccgc aacgagacag tct                43

<210> SEQ ID NO 26
<211> LENGTH: 43
<212> TYPE: DNA
<213> ORGANISM: Artificial Sequence
<220> FEATURE:
<223> OTHER INFORMATION: Synthetic construct

<400> SEQUENCE: 26
ccgagataat tccaccgttg gatccattcc agcagaacaa gat                43

<210> SEQ ID NO 27
<211> LENGTH: 21
<212> TYPE: DNA
<213> ORGANISM: Artificial Sequence
<220> FEATURE:
<223> OTHER INFORMATION: Synthetic construct

<400> SEQUENCE: 27
gatgtcacga aaaattccct c                                         21

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
gcaatccgag gatcgtcac                                            19

<210> SEQ ID NO 29
<211> LENGTH: 18
<212> TYPE: DNA
<213> ORGANISM: Artificial Sequence
<220> FEATURE:
<223> OTHER INFORMATION: Synthetic construct

<400> SEQUENCE: 29
tgcaaagcac gtggtgcc                                             18

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
acacaaactc cagagtgtag                                           20

<210> SEQ ID NO 31
<211> LENGTH: 46
<212> TYPE: DNA
<213> ORGANISM: Artificial Sequence
<220> FEATURE:
<223> OTHER INFORMATION: Synthetic construct

<400> SEQUENCE: 31
ctctgtgaac ggtcatcacc tcgatggctt gaaccgattg gtatgg                46

<210> SEQ ID NO 32
<211> LENGTH: 44
<212> TYPE: DNA
<213> ORGANISM: Artificial Sequence
<220> FEATURE:
<223> OTHER INFORMATION: Synthetic construct

<400> SEQUENCE: 32
cttacatggt aatatccagc gtgccacttc accactcgga gcac                  44

<210> SEQ ID NO 33
<211> LENGTH: 19
<212> TYPE: DNA
<213> ORGANISM: Artificial Sequence
<220> FEATURE:
<223> OTHER INFORMATION: Synthetic construct

<400> SEQUENCE: 33
gaacgtctcc cttcaatcc                                              19

<210> SEQ ID NO 34
<211> LENGTH: 19
<212> TYPE: DNA
<213> ORGANISM: Artificial Sequence
<220> FEATURE:
<223> OTHER INFORMATION: Synthetic construct

<400> SEQUENCE: 34
ggaccagaaa tccgtcaca                                              19

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
ccgactaccc acatcgttac                                             20

<210> SEQ ID NO 36
<211> LENGTH: 20
<212> TYPE: DNA
<213> ORGANISM: Artificial Sequence
<220> FEATURE:
<223> OTHER INFORMATION: Synthetic construct

<400> SEQUENCE: 36
accttgatgc taaggtggaa                                             20

<210> SEQ ID NO 37
<211> LENGTH: 44
<212> TYPE: DNA
<213> ORGANISM: Artificial Sequence
<220> FEATURE:
<223> OTHER INFORMATION: Synthetic construct

<400> SEQUENCE: 37
gattccactt ccaacgtcgt tgcataggca ttgtatccag agtg                  44

<210> SEQ ID NO 38
<211> LENGTH: 42

```
<212> TYPE: DNA
<213> ORGANISM: Artificial Sequence
<220> FEATURE:
<223> OTHER INFORMATION: Synthetic construct

<400> SEQUENCE: 38
cgaagtgaac cttgtcaaca tgagactacc cacatcgtta cc                          42

<210> SEQ ID NO 39
<211> LENGTH: 20
<212> TYPE: DNA
<213> ORGANISM: Artificial Sequence
<220> FEATURE:
<223> OTHER INFORMATION: Synthetic construct

<400> SEQUENCE: 39
agcaacatag gtttcagttc                                                   20

<210> SEQ ID NO 40
<211> LENGTH: 18
<212> TYPE: DNA
<213> ORGANISM: Artificial Sequence
<220> FEATURE:
<223> OTHER INFORMATION: Synthetic construct

<400> SEQUENCE: 40
ctgtgaacgg tcatcacc                                                     18

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
acggacatgt cgatcatgga                                                   20

<210> SEQ ID NO 42
<211> LENGTH: 22
<212> TYPE: DNA
<213> ORGANISM: Artificial Sequence
<220> FEATURE:
<223> OTHER INFORMATION: Synthetic construct

<400> SEQUENCE: 42
cgtctccctt caatccgatg gc                                                22

<210> SEQ ID NO 43
<211> LENGTH: 42
<212> TYPE: DNA
<213> ORGANISM: Artificial Sequence
<220> FEATURE:
<223> OTHER INFORMATION: Synthetic construct

<400> SEQUENCE: 43
atgggggatc atgtaactcg cctcgtcgtt tggtatggct tc                          42

<210> SEQ ID NO 44
<211> LENGTH: 41
<212> TYPE: DNA
<213> ORGANISM: Artificial Sequence
<220> FEATURE:
<223> OTHER INFORMATION: Synthetic construct

<400> SEQUENCE: 44
```

-continued

```
aagcggttag ctccttcggt ctgctgccat aaccatgagt g                    41
```

<210> SEQ ID NO 45
<211> LENGTH: 19
<212> TYPE: DNA
<213> ORGANISM: Artificial Sequence
<220> FEATURE:
<223> OTHER INFORMATION: Synthetic construct

<400> SEQUENCE: 45

```
ctacaggcat cgtggtgtc                                             19
```

<210> SEQ ID NO 46
<211> LENGTH: 20
<212> TYPE: DNA
<213> ORGANISM: Artificial Sequence
<220> FEATURE:
<223> OTHER INFORMATION: Synthetic construct

<400> SEQUENCE: 46

```
cttacggatg gcatgacagt                                            20
```

<210> SEQ ID NO 47
<211> LENGTH: 18
<212> TYPE: DNA
<213> ORGANISM: Artificial Sequence
<220> FEATURE:
<223> OTHER INFORMATION: Synthetic construct

<400> SEQUENCE: 47

```
tgggaaccgg agctgaat                                              18
```

<210> SEQ ID NO 48
<211> LENGTH: 25
<212> TYPE: DNA
<213> ORGANISM: Artificial Sequence
<220> FEATURE:
<223> OTHER INFORMATION: Synthetic construct

<400> SEQUENCE: 48

```
tccgatcgtt gtcagaagta agttg                                      25
```

<210> SEQ ID NO 49
<211> LENGTH: 48
<212> TYPE: DNA
<213> ORGANISM: Artificial Sequence
<220> FEATURE:
<223> OTHER INFORMATION: Synthetic construct

<400> SEQUENCE: 49

```
ccaaagagta aagtccttct ctctcgagag actgttggcc cttgaagg             48
```

<210> SEQ ID NO 50
<211> LENGTH: 47
<212> TYPE: DNA
<213> ORGANISM: Artificial Sequence
<220> FEATURE:
<223> OTHER INFORMATION: Synthetic construct

<400> SEQUENCE: 50

```
gtgttgatgt tatccaccttt ttgtggacta ggaaaacaga tcaatag             47
```

<210> SEQ ID NO 51
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 51
taatcctgga actccggtgc                                                    20

<210> SEQ ID NO 52
<211> LENGTH: 23
<212> TYPE: DNA
<213> ORGANISM: Artificial Sequence
<220> FEATURE:
<223> OTHER INFORMATION: Synthetic construct

<400> SEQUENCE: 52
tttatgccaa ttaacatttt gac                                                23

<210> SEQ ID NO 53
<211> LENGTH: 19
<212> TYPE: DNA
<213> ORGANISM: Artificial Sequence
<220> FEATURE:
<223> OTHER INFORMATION: Synthetic construct

<400> SEQUENCE: 53
atccacaggg aggagctct                                                     19

<210> SEQ ID NO 54
<211> LENGTH: 19
<212> TYPE: DNA
<213> ORGANISM: Artificial Sequence
<220> FEATURE:
<223> OTHER INFORMATION: Synthetic construct

<400> SEQUENCE: 54
ctccacctat aaaatcggc                                                     19

<210> SEQ ID NO 55
<211> LENGTH: 43
<212> TYPE: DNA
<213> ORGANISM: Artificial Sequence
<220> FEATURE:
<223> OTHER INFORMATION: Synthetic construct

<400> SEQUENCE: 55
gggcgtggta gcgcagacca gtcaagtgat cctcctgcct cag                          43

<210> SEQ ID NO 56
<211> LENGTH: 46
<212> TYPE: DNA
<213> ORGANISM: Artificial Sequence
<220> FEATURE:
<223> OTHER INFORMATION: Synthetic construct

<400> SEQUENCE: 56
gaggtttccc tatgttgccc aggcccaaag ttcaaggatc acttgg                       46

<210> SEQ ID NO 57
<211> LENGTH: 19
<212> TYPE: DNA
<213> ORGANISM: Artificial Sequence
<220> FEATURE:
<223> OTHER INFORMATION: Synthetic construct

<400> SEQUENCE: 57
cagcctcaac ctcctgggc                                                     19
```

```
<210> SEQ ID NO 58
<211> LENGTH: 20
<212> TYPE: DNA
<213> ORGANISM: Artificial Sequence
<220> FEATURE:
<223> OTHER INFORMATION: Synthetic construct

<400> SEQUENCE: 58
taatcccagc attttgggag                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic construct

<400> SEQUENCE: 59
ggtcccagct atttggaagg                                              20

<210> SEQ ID NO 60
<211> LENGTH: 19
<212> TYPE: DNA
<213> ORGANISM: Artificial Sequence
<220> FEATURE:
<223> OTHER INFORMATION: Synthetic construct

<400> SEQUENCE: 60
tggtcttgaa cttctgggc                                               19
```